(12) United States Patent
Lin et al.

(10) Patent No.: US 10,273,151 B2
(45) Date of Patent: Apr. 30, 2019

(54) SENSING DEVICE INCLUDING A MEMS SENSOR AND AN ADJUSTABLE AMPLIFIER

(71) Applicant: SILICON INTEGRATED SYSTEMS CORP., Hsinchu (TW)

(72) Inventors: Wen-Chi Lin, Hsinchu (TW); Ssu-Che Yang, Hsinchu (TW); Keng-Nan Chen, Hsinchu (TW)

(73) Assignee: SILICON INTEGRATED SYSTEMS CORP., Hsinchu (TW)

( * ) Notice: Subject to any disclaimer, the term of this patent is extended or adjusted under 35 U.S.C. 154(b) by 0 days.

(21) Appl. No.: 15/828,044

(22) Filed: Nov. 30, 2017

(65) Prior Publication Data

US 2018/0155187 A1 Jun. 7, 2018

(30) Foreign Application Priority Data

Dec. 2, 2016 (TW) .............................. 105140006 A

(51) Int. Cl.
| | |
|---|---|
| *B81B 7/00* | (2006.01) |
| *B81B 7/02* | (2006.01) |
| *B81C 1/00* | (2006.01) |
| *G05F 3/02* | (2006.01) |
| *H02M 3/07* | (2006.01) |
| *H03H 9/10* | (2006.01) |
| *G06G 7/184* | (2006.01) |
| *G01N 27/414* | (2006.01) |
| *G01P 15/125* | (2006.01) |

(52) U.S. Cl.
CPC ................ *B81B 7/02* (2013.01); *B81B 7/007* (2013.01); *B81C 1/00301* (2013.01); *G01P 15/125* (2013.01); *G05F 3/02* (2013.01); *G06G 7/184* (2013.01); *H02M 3/073* (2013.01); *B81B 2201/02* (2013.01); *G01N 27/4148* (2013.01); *H03H 9/1057* (2013.01)

(58) Field of Classification Search
CPC .. H02M 1/08; H02M 1/32; H02M 2001/0009; H02M 3/158; G05F 1/575
USPC ........................................................ 257/415
See application file for complete search history.

(56) References Cited

U.S. PATENT DOCUMENTS

| | | | | |
|---|---|---|---|---|
| 9,800,212 | B2 * | 10/2017 | Barbieri | .............. H03F 3/45273 |
| 2008/0100274 | A1 * | 5/2008 | Hayakawa | .............. H02M 1/36 323/284 |
| 2009/0179706 | A1 * | 7/2009 | Wong | .................... H03F 1/0205 330/311 |

(Continued)

*Primary Examiner* — Andy Huynh
(74) *Attorney, Agent, or Firm* — Maschoff Brennan

(57) ABSTRACT

A sensing device includes a MEMS sensor and an adjustable amplifier. The MEMS sensor is configured to generate an input signal according to environmental changes. The adjustable amplifier has a first input terminal, a second input terminal, a third input terminal, a fourth input terminal and a first output terminal. The first input terminal is electrically connected to the MEMS sensor for receiving the input signal. The second input terminal is electrically connected to a first signal terminal for receiving a first common-mode signal. The third input terminal is electrically connected to the first output terminal. The fourth input terminal is electrically connected to a second signal terminal. An electric potential of a first output signal output by the first output terminal of the adjustable amplifier is related to electric potentials of the input signal, the first signal terminal and the second signal terminal.

8 Claims, 6 Drawing Sheets

(56) References Cited

U.S. PATENT DOCUMENTS

2017/0207760 A1\* 7/2017 Werking ............ H03F 3/45475
2017/0359036 A1\* 12/2017 Frohlich .................. H03F 3/04

\* cited by examiner

SENSING DEVICE INCLUDING A MEMS SENSOR AND AN ADJUSTABLE AMPLIFIER

CROSS-REFERENCE TO RELATED APPLICATIONS

This non-provisional application claims priority under 35 U.S.C. § 119(a) on Patent Application No(s). 105140006 filed in Taiwan, R.O.C. on Dec. 2, 2016, the entire contents of which are hereby incorporated by reference.

TECHNICAL FIELD

The disclosure relates to sensing device, more particularly to a sensing device using MEMS sensor.

BACKGROUND

With development of technology and people's attention to audio-visual entertainment, the application of digital microphones becomes widespread. The uses of digital microphones are essential no matter in public places (e.g. corporate meeting rooms, public exhibition places) or private places (personal audio-visual rooms). In general, a Microelectromechanical Systems (MEMS) and an Application Specific Integrated Circuit (ASIC) are disposed in an internal circuit of a digital microphone. A source follower, a Programmable Gain Amplifier (PGA) and an Analog to Digital converter (ADC) are used for processing or buffering an electric signal so as to convert the electric signal to a digital signal after the electric signal obtained by the MEMS sensor for achieving a high signal-to-noise ratio (SNR). However, this kind of circuit coming with the source follower, the PGA and the ADC consumes a huge amount of current and occupies a space in a circuit.

SUMMARY

According to one embodiment of the present disclosure, a sensing device is disclosed. The sensing device comprises a MEMS sensor and an adjustable amplifier. The MEMS sensor is configured to generate an input signal according to an environmental change. The adjustable amplifier has a first input terminal, a second input terminal, a third input terminal, a fourth input terminal and a first output terminal. The first input terminal of the adjustable amplifier is electrically connected to the MEMS sensor and configured to receive the input signal. The second input terminal is electrically connected to the first signal terminal and configured to receive a first common-mode signal. The third input terminal is electrically connected to the first output terminal. The fourth input terminal is electrically connected to a second signal terminal. An electric potential of the first output signal output from the first output terminal of the adjustable amplifier is related to an electric potential of the input signal, an electric potential of first signal terminal and an electric potential of second signal terminal.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1:
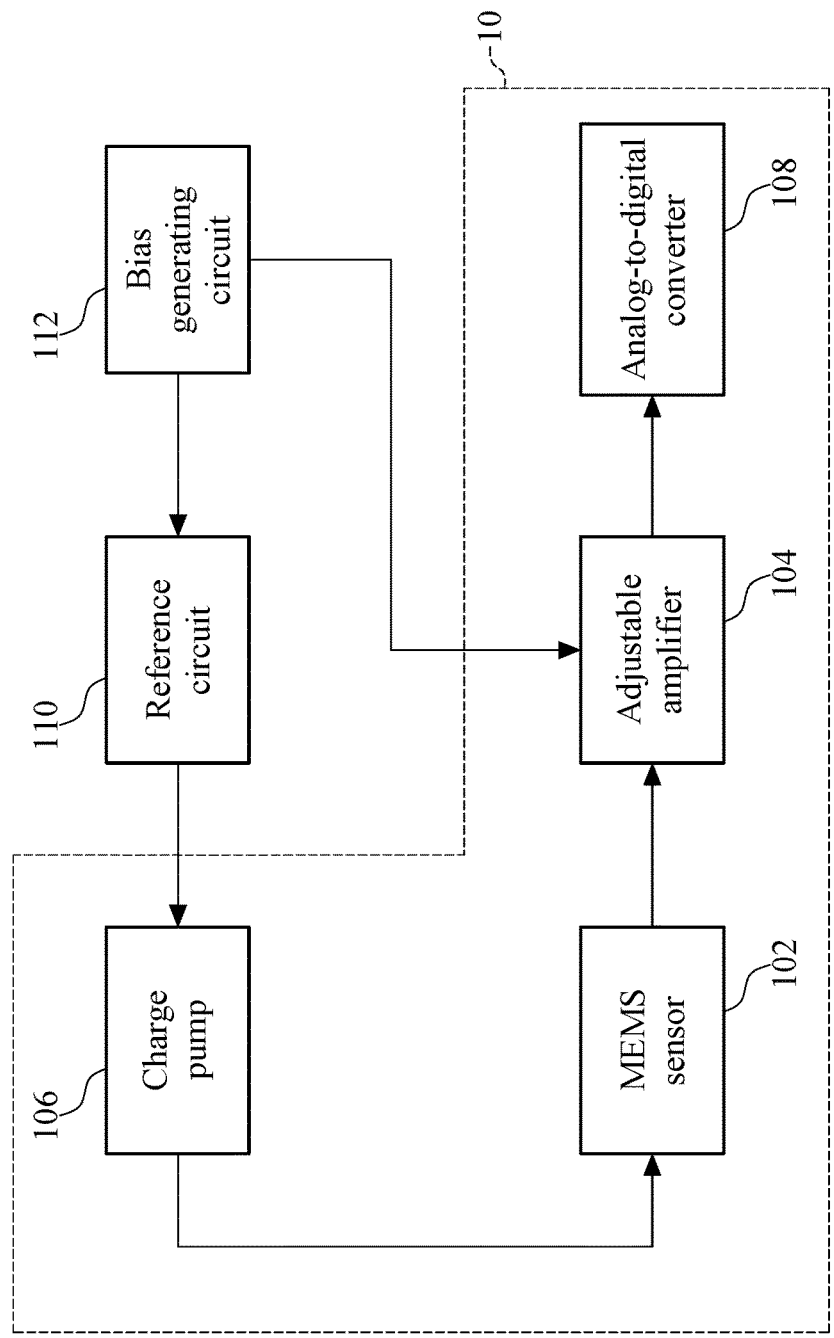
FIG. 1 is a block diagram of a sensing device according to one embodiment of the present disclosure.

Please refer to FIG. 1, which is a block diagram of a sensing device according to one embodiment of the present disclosure. The sensing device 10 includes a MEMS sensor 102 and an adjustable amplifier 104. The MEMS sensor 102 is configured to generate an input signal according to an environmental change (e.g. sound inflection). In an example, the MEMS sensor 102 is implemented via a capacitor including a diaphragm and a backplane, with the capacitor having a dielectric layer formed by air. The diaphragm is formed by a thin and low-stress layer consisting of poly-Si or silicon nitride, and the backplane is formed by a thick layer consisting of poly-Si or metals. The capacitor structure of the MEMS sensor 102 may be used for converting the detected sound pressure to capacitance variation, and further generating an electrical signal according to the capacitance variation. The electrical signal is considered as the input signal as described above.

Figure 2:
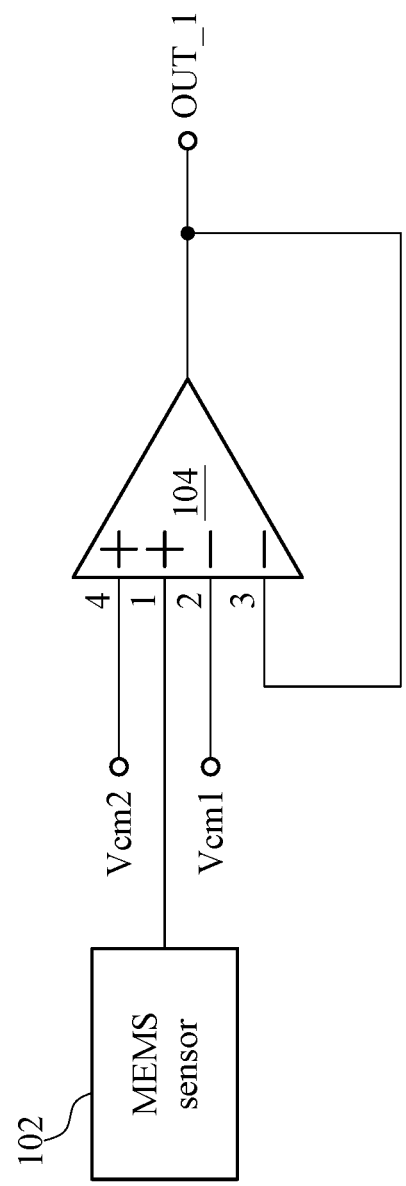
FIG. 2 is a circuit diagram of a sensing device according to one embodiment of the present disclosure.

Please refer to FIG. 1 and FIG. 2. FIG. 2 is a circuit diagram of a sensing device according to one embodiment of the present disclosure. As shown in FIG. 2, the adjustable amplifier 104 has a first input terminal 1, a second input terminal 2, a third input terminal 3, a fourth input terminal 4 and a first output terminal OUT_1. The first input terminal 1 is electrically connected to the MEMS sensor 102 and configured to receive the input signal from the MEMS sensor 102. The second input terminal 2 is electrically connected to the first signal terminal Vcm1 and configured to receive a first common-mode signal from the first signal terminal Vcm1. The third input terminal 3 is electrically connected to the first output terminal OUT_1. The fourth input terminal 4 is electrically connected to the second signal terminal Vcm2. An electric potential of the first output signal output from the first output terminal OUT_1 of the adjustable amplifier 104 is related to an electric potential of the input signal, an electric potential of the first signal terminal Vcm1 and an electric potential of the second signal terminal Vcm2. In this embodiment, the electric potential of the first signal terminal Vcm1 is the same as the electric potential of the second signal terminal Vcm2. In the sensing device 10 of the present disclosure, since the adjustable amplifier 104 has a feature of high impedance input, the current consumption may be reduced while the MEMS sensor 102 is directly coupled to a high impedance input terminal (first input terminal 1) of the adjustable amplifier

104. Furthermore, in the sensing device 10 of the present disclosure, the circuit is more compact and thus the space for arrangement is saved. Moreover, a high signal-to-noise ratio (SNR) may be achieved as the MEMS sensor 102 is directly coupled with the adjustable amplifier 104 without disposing a source follower between them.

Please refer back to FIG. 1. In an example, the sensing device 10 further includes a charge pump 106 and an analog-to-digital converter 108. The charge pump 106 is electrically connected to the MEMS sensor 102. The charge pump 106 is configured to supply a reference voltage, so that the MEMS sensor is capable of generating the input signal according to the environmental change and the reference voltage. In one embodiment, the MEMS sensor generates the input signal according to the environmental change and the reference voltage. The analog-to-digital converter 108 is electrically connected to the first output terminal OUT_1 of the adjustable amplifier 104 and configured to convert the first output signal from an analog form into a digital form. In other words, the first output signal output by the first output terminal OUT_1 of the adjustable amplifier 104 is an analog signal, and the first output signal output becomes a digital signal via the operation of the analog-to-digital converter 108. The first output signal in digital form may be further supplied to an external circuit. In a practical example, the sensing device 10 may be further coupled with a reference circuit 110 and a bias generating circuit 112 since the sensing device 10 is adapted to a digital microphone.

Figure 3:
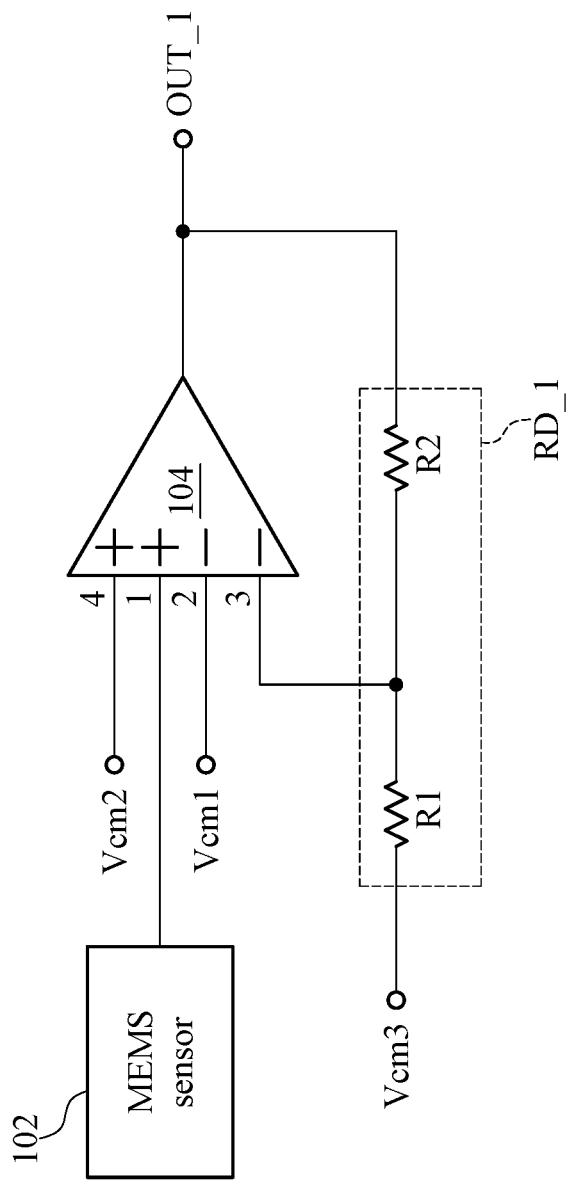
FIG. 3 is a circuit diagram of a sensing device according to another embodiment of the present disclosure.

Please refer to FIG. 1 and FIG. 3. FIG. 3 is a circuit diagram of a sensing device according to another embodiment of the present disclosure. Comparing to the embodiment of FIG. 2, the sensing device 10 shown in FIG. 3 further includes a first resistor set RD_1. The first resistor set RD_1 includes a first resistor R1 and a second resistor R2. A first terminal of the first resistor R1 is electrically connected to a third signal terminal Vcm3 supplying a third common-mode signal. A second terminal of the first resistor R1 is electrically connected to the third input terminal 3. A first terminal of the second resistor R2 is electrically connected to the third input terminal 3, and a second terminal of the second resistor R2 is electrically connected to the first output terminal OUT_1. In practice, the first resistor set RD_1 is used for adjusting the first output signal. Specifically, the electric potential of the first output signal may be adjusted by changing the resistances of the first resistor R1 and the second resistor R2 within the first resistor set RD_1. In this embodiment, the electric potential of the second signal terminal Vcm2 is the same as the electric potential of the third signal terminal Vcm3.

Figure 4:
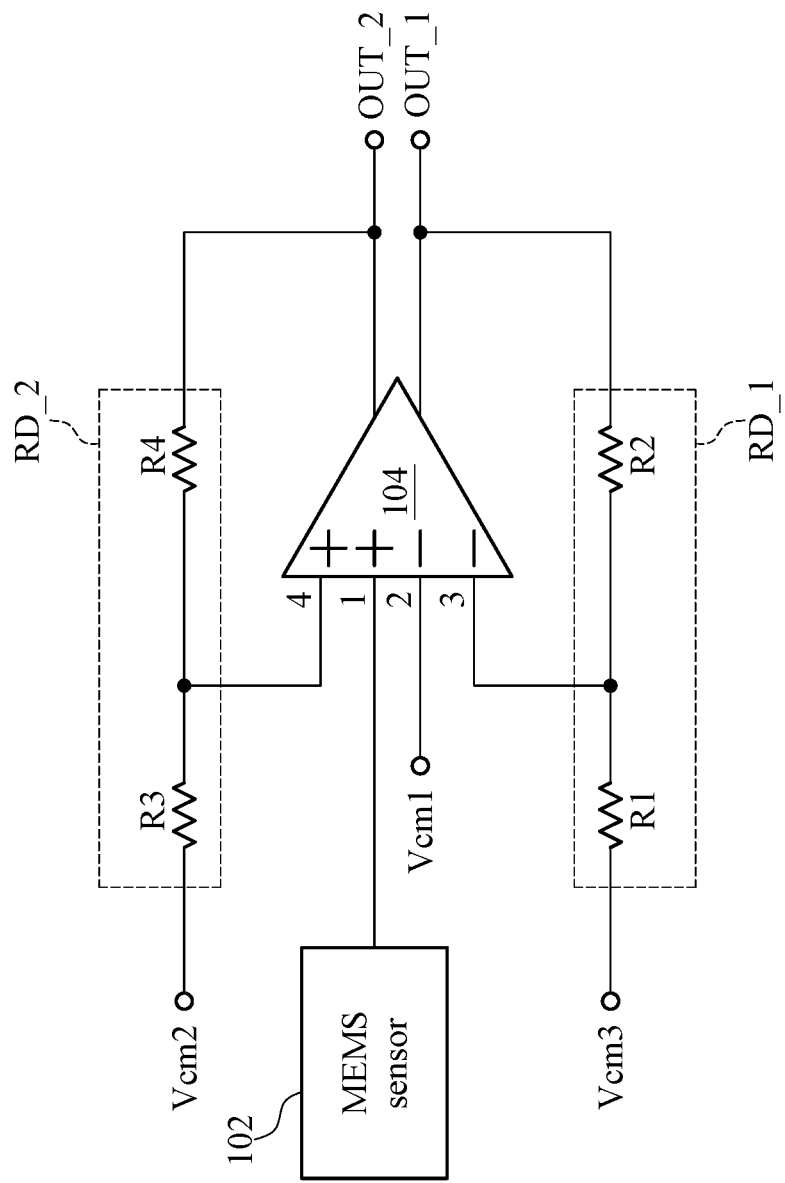
FIG. 4 is a circuit diagram of a sensing device according to another embodiment of the present disclosure.

Please refer to FIG. 1 and FIG. 4. FIG. 4 is a circuit diagram of a sensing device according to another embodiment of the present disclosure. Comparing to the embodiment of FIG. 3, the adjustable amplifier 104 shown in FIG. 4 further has a second output terminal OUT_2 as well as a second resistor set RD_2. The second resistor set RD_2 includes a third resistor R3 and a fourth resistor R4. A first terminal of the third resistor R3 is electrically connected to a second signal terminal Vcm2, and a second terminal of the third resistor R3 is electrically connected to the fourth input terminal 4. A first terminal of the fourth resistor R4 is electrically connected to the fourth input terminal 4, and a second terminal of the fourth resistor R4 is electrically connected to the second output terminal OUT_2. The electric potential of the second signal terminal Vcm2 is the same as the electric potential of the third signal terminal Vcm3. In the embodiment of FIG. 4, the first resistor R1 and the second resistor R2 coupled with the third input terminal 3 as well as the third resistor R3 and the fourth resistor R4 coupled with the fourth input terminal 4 may be used for adjusting the electric potentials of the first output terminal OUT_1 and the second output terminal OUT_2 according to actual demands. The first input terminal 1 is used for supplying a high impedance input to the MEMS sensor 102. Therefore, it is not necessary to dispose a source follower between the MEMS sensor 102 and the adjustable amplifier 104.

Figure 5:
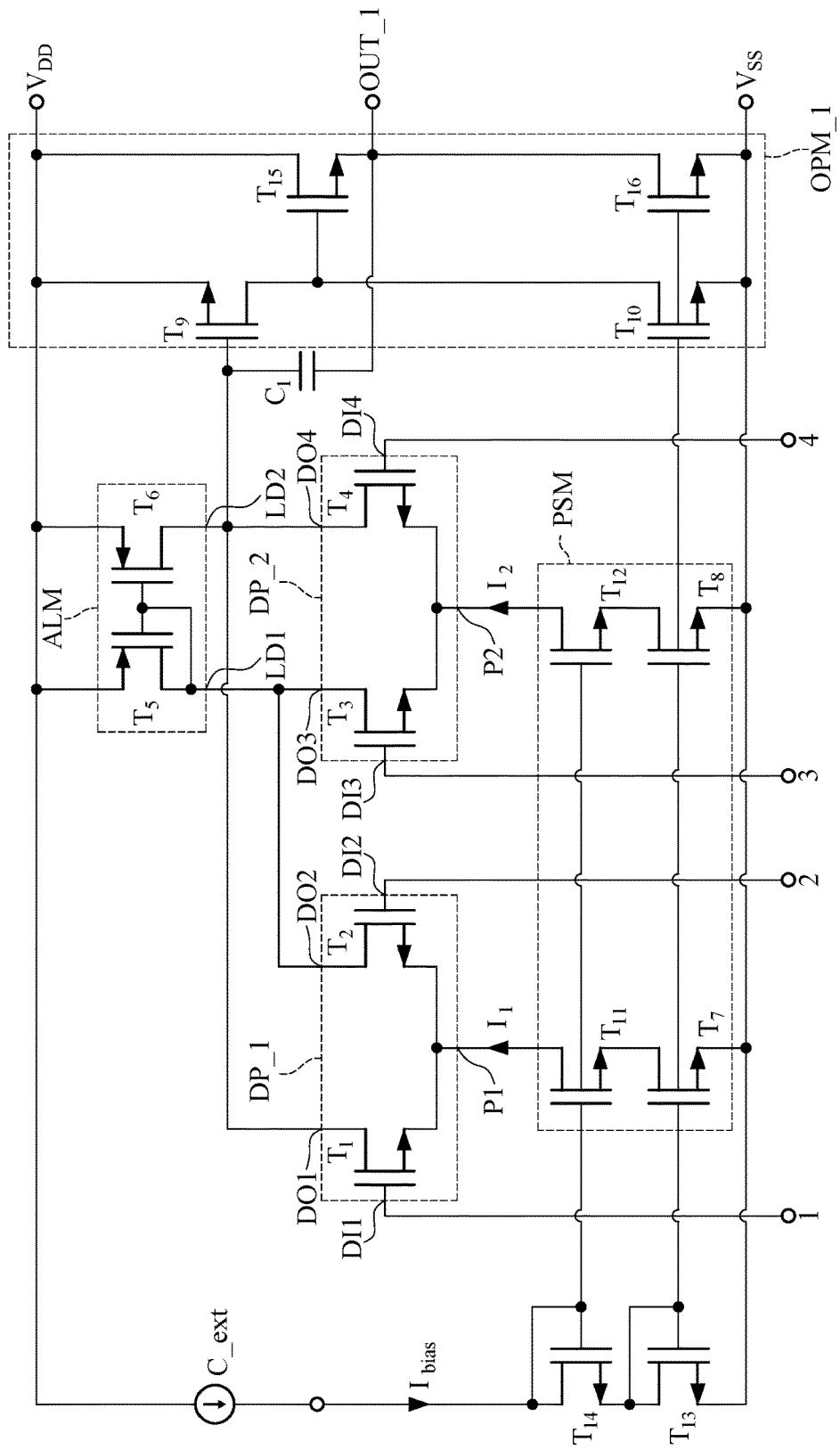
FIG. 5 is an internal circuit diagram of an adjustable amplifier according to one embodiment of the present disclosure.

Please refer to FIG. 5, which is an internal circuit diagram of an adjustable amplifier according to one embodiment of the present disclosure. The adjustable amplifier shown in FIG. 5 corresponds to adjustable amplifier 104 shown in FIG. 2. The adjustable amplifier 104 includes an active loading module ALM, a first differential pair DP_1, a second differential pair DP_2 and a power module PSM. The active loading module ALM has a first loading terminal LD1 and a second loading terminal LD2. A first differential pair DP_1 has a first differential input terminal DI1, a second differential input terminal DI2, a first differential output terminal DO1, a second differential output terminal DO2 and a first power terminal P1. The first differential input terminal DI1 receives the input signal from the first input terminal 1, and the second differential input terminal DI2 receives the first common-mode signal from the second input terminal 2. The first differential output terminal DO1 is electrically connected to the second loading terminal LD2. The second differential output terminal DO2 is electrically connected to the first loading terminal LD1. In one embodiment, as shown in FIG. 5, the second differential pair DP_2 has a third differential input terminal DI3, a fourth differential input terminal DI4, a third differential output terminal DO3, a fourth differential output terminal DO4 and a second power terminal P2. The third differential input terminal DI3 is electrically connected to the first output terminal OUT_1. The fourth differential input terminal DI4 receives the second common-mode signal from the fourth input terminal 4. The third differential output terminal DO3 is electrically connected to the first loading terminal LD1. The fourth differential output terminal DO4 is electrically connected to the second loading terminal LD2. In practice, the first differential pair DP_1 and the second differential pair DP_2 are used for amplifying the received signal. For example, when a pair of signals received by the differential pairs is a differential-mode signal (same amplitude/inverting phase), the current of the signal becomes double. On the contrary, when a pair of signals received by the differential pairs is a common-mode signal (same amplitude/phase), the current of the signal is cancelled off. In general, noise is considered as the common-mode signal.

The power module PSM is electrically connected to the first power terminal P1, the second power terminal P2 and the first reference voltage Vss. The power module PSM is configured to supply the first current I1 to the first differential pair DP_1 through the first power terminal P1. The power module PSM is configured to supply the second current I2 to the second differential pair DP_2 through the second power terminal P2. The power module PSM includes transistors T7-T8 and transistors T11-T12. The power module PSM may be used for adjusting at least one of the first current I1 and the second current I2. As shown in FIG. 5, the transistor T14 receives the input current Ibias of the current source C_ext and the transistor T14 is combined with the transistor T11 to form a current mirror. The transistor T13 is combined with the transistor T7 to form another current mirror. The first current I1 is mapped out by those two current mirrors. Similarly, the transistor T14 is combined with the transistor T12 to form a current mirror, and the transistor T13 is combined with the transistor T8 to form another current mirror. The second current I2 is mapped out by those two current mirrors.

In one embodiment, the first differential pair DP_1 includes a first transistor T1 and a second transistor T2. A first terminal of the first transistor T1 is electrically connected to the second loading terminal LD2, and a second terminal of the first transistor T1 is electrically connected to the power module PSM. A control terminal of the first transistor T1 receives the input signal. A first terminal of the second transistor T2 is electrically connected to the first loading terminal LD1, and a second terminal of the second transistor T2 is electrically connected to the power module PSM. A control terminal of the second transistor T2 receives the first common-mode signal. In one embodiment, the second differential pair DP_2 includes a third transistor T3 and a fourth transistor T4. A first terminal of the third transistor T3 is electrically connected to the first loading terminal LD1, and a second terminal of the third transistor T3 is electrically connected to the power module PSM. A control terminal of the third transistor T3 receives the first output signal. A first terminal of the fourth transistor T4 is electrically connected to the second loading terminal LD2, and a second terminal of the fourth transistor T4 is electrically connected to the power module PSM. A control terminal of the fourth transistor T4 receives the second common-mode signal.

Figure 6:
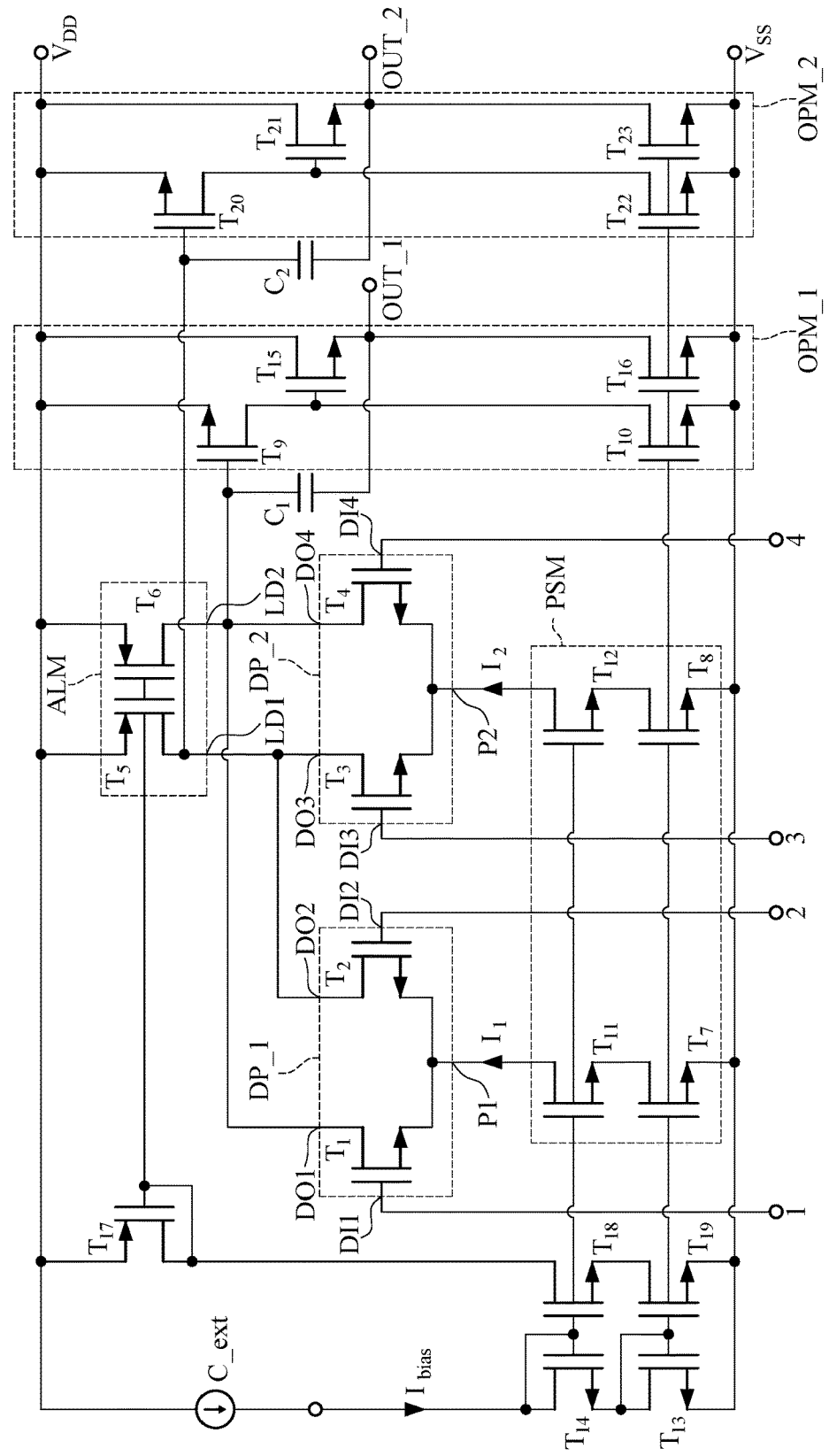
FIG. 6 is an internal circuit diagram of an adjustable amplifier according to another embodiment of the present disclosure.

In one embodiment, the active loading module ALM includes a fifth transistor T5 and a sixth transistor T6. A first terminal of the fifth transistor T5 is configured to receive the first operating voltage VDD, and a second terminal of the fifth transistor T5 is electrically connected to the first loading terminal LD1. A control terminal of the fifth transistor T5 is electrically connected to the first loading terminal LD1. A first terminal of the sixth transistor T6 is configured to receive the first operating voltage VDD and a second terminal of the sixth transistor T6 is electrically connected to the second loading terminal LD2. A control terminal of the sixth transistor T6 is electrically connected to the first loading terminal LD1. The fifth transistor T5 is combined with the sixth transistor T6 to form a current mirror. In general, it is not proper to use resistors as a load within an integrated circuit. Therefore, in this case, a gate and a drain of the fifth transistor T5 are connected together to form an active load. In practice, as shown in FIG. 5, the adjustable amplifier 104 further includes a first output module OPM_1. In the first output module OPM_1, a control terminal of the transistor T9 is electrically connected to the second loading terminal LD2, a first terminal of the transistor T9 is configured to receive the first operating voltage VDD. The transistor T10 is combined with the transistor T13 to form a current mirror, and the transistor T16 is combined with the transistor T13 to form another current mirror. A control terminal of the transistor T15 is electrically connected to a second terminal of the transistor T9. A first terminal of the transistor T15 receives the first operating voltage VDD, and a second terminal of the transistor T15 is electrically connected to the first output terminal OUT_1. Please refer to FIG. 6, which is an internal circuit diagram of an adjustable amplifier according to another embodiment of the present disclosure. The adjustable amplifier shown in FIG. 6 corresponds to the adjustable amplifier 104 shown in FIG. 4. Comparing to FIG. 5, the circuit shown in FIG. 6 comes with two output terminals, which are the first output terminal OUT_1 and the second output terminal OUT_2. Moreover, the circuit shown in FIG. 6 further includes transistor T17-T19 as well as the second output module OPM_2. The transistor T17 is combined with the transistor T6 to form a current mirror, and the transistor T5 is combined with the transistor T6 to form another current mirror. The second output module OPM_2 includes transistor T20-T23, and their connections and operations are similar to that of the first output module OPM_1, so not repeated here. It is noted that the circuit shown in FIG. 6 comes with two output terminals (the first output terminal OUT_1 and the second output terminal OUT_2), so persons having ordinary skills in the art are able to realize that the circuit shown in FIG. 6 needs a common-mode feedback circuit, not shown in FIG. 6.

Based on the above descriptions, in the sensing device of the present disclosure, the MEMS sensor is directly coupled with the adjustable amplifier having the high impedance input without disposing a source follower for buffering. The current consumption is reduced due to the high impedance input of the adjustable amplifier. Moreover, n the sensing device of the present disclosure, the utilization of the circuit board is improved and the signal with a high SNR may be output for external circuits.

What is claimed is:
1. A sensing device, comprising:
a MEMS sensor configured to generate an input signal according to an environment change; and
an adjustable amplifier having a first input terminal, a second input terminal, a third input terminal, a fourth input terminal and a first output terminal, with the first input terminal electrically connected to the MEMS sensor and receiving the input signal from the MEMS sensor, the second input terminal electrically connected to a first signal terminal and receiving a first common-mode signal from the first signal terminal, the third input terminal electrically connected to the first output terminal, the fourth input terminal electrically connected to a second signal terminal, and an electric potential of the second signal terminal is the same as an electric potential of the first signal terminal;
wherein an electric potential of a first output signal output from the first output terminal of the adjustable amplifier is related to all of an electric potential of the input signal, the electric potential of the first signal terminal and the electric potential of the second signal terminal.
2. The sensing device according to claim 1, further comprising a first resistor set comprising:
a first resistor, with a first terminal of the first resistor electrically connected to a third signal terminal configured to provide a third common-mode signal, a second terminal of the first resistor electrically connected to the third input terminal; and
a second resistor, with a first terminal of the second resistor electrically connected to the third input terminal, a second terminal of the second resistor electrically connected to the first output terminal.
3. The sensing device according to claim 2, wherein the adjustable amplifier further has a second output terminal and the sensing device further comprises a second resistor set comprising:
a third resistor, with a first terminal of the third resistor electrically connected to the second signal terminal, and a second terminal of the third resistor electrically connected to the fourth input terminal; and
a fourth resistor, with a first terminal of the fourth resistor electrically connected to the fourth input terminal, and a second terminal of the fourth resistor electrically connected to the second output terminal.

4. The sensing device according to claim 1, wherein the adjustable amplifier comprises:
- an active loading module having a first loading terminal and a second loading terminal;
- a first differential pair having a first differential input terminal, a second differential input terminal, a first differential output terminal, a second differential output terminal and a first power terminal, the first differential input terminal receiving the input signal from the first input terminal, the second differential input terminal receiving the first common-mode signal from the second input terminal, the first differential output terminal electrically connected to the second loading terminal, and the second differential output terminal electrically connected to the first loading terminal;
- a second differential pair having a third differential input terminal, a fourth differential input terminal, a third differential output terminal, a fourth differential output terminal and a second power terminal, the third differential input terminal electrically connected to the first output terminal, the fourth differential input terminal receiving a second common-mode signal from the fourth input terminal, the third differential output terminal electrically connected to the first loading terminal and the fourth differential output terminal electrically connected to the second loading terminal; and
- a power module electrically connected to the first power terminal and the second power terminal, with the power module configured to supply a first current to the first differential pair through the first power terminal and to supply a second current to the second differential pair through the second power terminal;
- wherein the power module is configured to regulate at least one of the first current and the second current.

5. The sensing device according to claim 4, wherein the first differential pair comprises:
- a first transistor, with a first terminal of the first transistor electrically connected to the second loading terminal, a second terminal of the first transistor electrically connected to the power module, and a control terminal of the first transistor receiving the input signal; and
- a second transistor, with a first terminal of the second transistor electrically connected to the first loading terminal, a second terminal of the second transistor electrically connected to the power module, and a control terminal of the second transistor receiving the first common-mode signal.

6. The sensing device according to claim 4, wherein the second differential pair comprises:
- a third transistor, with a first terminal of the third transistor electrically connected to the first loading terminal, a second terminal of the third transistor electrically connected to the power module, and a control terminal of the third transistor receiving the first output signal; and
- a fourth transistor, with a first terminal of the fourth transistor electrically connected to the second loading terminal, a second terminal of the fourth transistor electrically connected to the power module, a control terminal of the fourth transistor receiving the second common-mode signal.

7. The sensing device according to claim 4, wherein the active loading module comprises:
- a fifth transistor, with a first terminal of the fifth transistor configured to receive a first operating voltage, a second terminal of the fifth transistor electrically connected to the first loading terminal, and a control terminal of the fifth transistor electrically connected to the first loading terminal; and
- a sixth transistor, with a first terminal of the sixth transistor configured to receive the first operating voltage, a second terminal of the sixth transistor electrically connected to the second loading terminal, and a control terminal of the sixth transistor electrically connected to the first loading terminal.

8. The sensing device according to claim 1, further comprising:
- a charge pump electrically connected to the MEMS sensor, with the charge pump configured to supply a reference voltage, the MEMS sensor generating the input signal according to an environmental change and the reference voltage; and
- an analog-to-digital converter electrically connected to the first output terminal of the adjustable amplifier and configured to convert the first output signal from an analog form into a digital form.

* * * * *